(12) United States Patent
Rahilly et al.

(10) Patent No.: US 11,304,345 B2
(45) Date of Patent: Apr. 12, 2022

(54) SUPPLY STATION WITH DOOR SHIELD

(71) Applicant: CareFusion 303, Inc., San Diego, CA (US)

(72) Inventors: Michael Rahilly, Encinitas, CA (US); Edward Stephen Ferner, Jr., Escondido, CA (US); Brendan John Burgess, Poway, CA (US); Scott Riley, Poway, CA (US); Michael Dugan Joyce, Chula Vista, CA (US); Noe Arroyo, National City, CA (US); Chris Pedersen, Santee, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 16/991,654

(22) Filed: Aug. 12, 2020

(65) Prior Publication Data
US 2020/0375072 A1 Nov. 26, 2020

Related U.S. Application Data

(63) Continuation of application No. 16/536,394, filed on Aug. 9, 2019, now Pat. No. 10,785,899, which is a
(Continued)

(51) Int. Cl.
*H05K 9/00* (2006.01)
*A61B 50/10* (2016.01)
*G06K 17/00* (2006.01)

(52) U.S. Cl.
CPC .......... *H05K 9/0016* (2013.01); *A61B 50/10* (2016.02); *G06K 17/0029* (2013.01);
(Continued)

(58) Field of Classification Search
USPC ................................. 361/728, 752, 816, 818
See application file for complete search history.

(56) References Cited

U.S. PATENT DOCUMENTS

| 4,677,251 A | 6/1987 | Merewether |
| 4,929,802 A | 5/1990 | Schaepers |
(Continued)

FOREIGN PATENT DOCUMENTS

| CN | 207097134 | 3/2018 |
| GB | 2183920 | 6/1987 |

OTHER PUBLICATIONS

International Search Report and Written Opinion for Application No. PCT/US2019/030378, dated Jul. 16, 2019, 18 pages.
(Continued)

*Primary Examiner* — Hung S. Bui
(74) *Attorney, Agent, or Firm* — Morgan, Lewis & Bockius LLP

(57) ABSTRACT

A door assembly is described. The door assembly includes a door structure that is mounted over an opening of an enclosure. The door structure includes a body that includes a first surface and a second surface opposite to the first surface. The first surface may face an inside of the enclosure when the door structure is closed. The door structure includes a number of finger bracket structures mounted on the first surface. Each one of the finger bracket structures includes a bracket and one or more finger gaskets coupled to the bracket. The finger gaskets of the finger bracket structures may contact enclosure brackets mounted around an edge of the opening of the enclosure when the door structure is closed. A combination of the finger gaskets in contact with enclosure brackets may create an electromagnetic interference (EMI) shield at the edge of the opening of the enclosure.

18 Claims, 9 Drawing Sheets

Related U.S. Application Data continuation of application No. 15/977,758, filed on May 11, 2018, now Pat. No. 10,420,258.

(52) U.S. Cl.
CPC .......... *H05K 9/0009* (2013.01); *H05K 9/0015* (2013.01); *A61B 2050/105* (2016.02)

(56) References Cited

U.S. PATENT DOCUMENTS

| | | | |
|---|---|---|---|
| 5,004,866 A * | 4/1991 | Cooke | G06F 1/182 |
| | | | 174/366 |
| 5,029,254 A * | 7/1991 | Stickney | H02B 1/16 |
| | | | 174/354 |
| 5,223,670 A | 6/1993 | Hogan | |
| 5,256,833 A | 10/1993 | Schwenk | |
| 5,894,106 A | 4/1999 | Schwenk et al. | |
| 6,120,304 A | 9/2000 | Harwood | |
| 6,303,854 B1 * | 10/2001 | Papaleo | H05K 9/0015 |
| | | | 174/382 |
| 6,384,323 B2 * | 5/2002 | Elm | H02B 1/30 |
| | | | 174/374 |
| 6,483,023 B1 * | 11/2002 | Jacques | H05K 7/1425 |
| | | | 174/358 |
| 10,420,258 B1 | 9/2019 | Rahilly | |
| 2010/0208433 A1 | 8/2010 | Heimann | |
| 2014/0197236 A1 | 7/2014 | Shoenfeld | |
| 2014/0216806 A1 * | 8/2014 | Poulsen | H05K 9/0015 |
| | | | 174/351 |
| 2017/0196128 A1 | 7/2017 | Elizondo, II | |
| 2018/0062729 A1 | 3/2018 | Linehan | |

OTHER PUBLICATIONS

Molyneux, Child J W, "EMC—Comparative Merits of Beryllium Copper", Electronic Engineering, Morgan-Grampian Ltd., London, GB, vol. 64, No. 784, Apr. 1, 1992, p. 19, 21, XP000291113, ISSN: 0013-4902.

* cited by examiner

SUPPLY STATION WITH DOOR SHIELD

CROSS-REFERENCE TO RELATED APPLICATION

This is a continuation of U.S. patent application Ser. No. 16/536,394, filed on Aug. 9, 2019, entitled "SUPPLY STATION WITH DOOR SHIELD," which issued as U.S. Pat. No. 10,785,899, on Sep. 22, 2020, which is a continuation of U.S. patent application Ser. No. 15/977,758, filed on May 11, 2018, entitled "SUPPLY STATION WITH DOOR SHIELD," which issued as U.S. Pat. No. 10,420,258 on Sep. 17, 2019, the disclosures of which are hereby incorporated by reference in their entirety for all purposes.

FIELD OF THE INVENTION

The present invention generally relates to supply stations that are equipped for reading radio-frequency identification ("RFID") tags and more particularly relates to supply stations with doors that shield radio frequency ("RF") signals.

BACKGROUND

Supply stations such as supply cabinets may be used for storing medical supplies. Medical supplies may be equipped with RFID tags and the supply cabinet may be equipped with RF transceivers to transmit RF signals to read RFID tags of medical supplies. In response to transmit RF signals, the RF transceiver may detect received RF signals from the RFID tags to generate an inventory list of the medical supplies. Every time the medical supply door is closed the RF transmitter may transmit RF signals to read the RFID tags of remaining medical supplies to update the inventory list.

SUMMARY

In some instances, the RF signal may leak outside the supply cabinet or the transceiver may receive RF signals from outside the supply cabinet. As a result, the RF transceiver can read RFID tags of items outside the supply cabinet or even may read the RFID tags of items in neighboring supply cabinets. Therefore, it is desirable to seal the medical supply cabinet against RF signals going out or coming in. In order to seal the supply cabinet the body of the supply cabinet may be made of a material that attenuates RF signals. A door of the supply cabinet can also be made of a material to limit, restrict, or prevent RF signals from passing through it. It is also desirable to limit, restrict, or prevent RF signal leakage from the openings between the door of the supply cabinet and the supply cabinet body.

In many instances, it is desirable to generate an inventory list of the supply items, such as medical supplies, that may exist in a supply cabinet. For example, the inventory list may be generated when the supply cabinet door closes. The supply items may be equipped with RFID tags or other tags that may be queried by sending RF signals. The supply cabinet may be equipped with a transceiver that may include a detector, a processor, and a memory, and the transceiver may send and receive RF signals to read the tags and to generate the inventory list. In these instances, it is desirable that RF signals do not leak to outside of the supply cabinet and, in particular, RF signals may not leak from outside to inside of the supply cabinet. Therefore, by electromagnetic interference ("EMI") shielding the supply cabinet when the supply cabinet door closes, the transceiver may generate an inventory list of supply items inside the supply cabinet.

According to various aspects of the subject technology, a shield assembly is provided. The shield assembly includes a closing structure configured to be mounted over an opening of an electromagnetic interference (EMI) shielded enclosure. The closing structure includes an inner surface configured to face an inside of the EMI shielded enclosure when the closing structure is closed and a finger bracket structure mounted on the inner surface, the finger bracket structure comprising a bracket and one or more finger gaskets coupled to the bracket. The shield assembly also includes an EMI shielded gasket having a rod coupled to a frame disposed around the opening of the EMI shielded enclosure.

According to various aspects of the subject technology, a method of sealing radio frequency (RF) signals inside an electromagnetic interference (EMI) shielded enclosure is provided. The method includes configuring a closing structure to be mounted over an opening of the EMI shielded enclosure, wherein the closing structure comprises an inner surface, facing the inner surface to an inside of the EMI shielded enclosure when the closing structure closes, mounting a finger bracket structure to the inner surface, wherein the finger bracket structure includes a bracket and one or more finger gaskets coupled to the bracket, mounting a frame around the opening of the EMI shielded enclosure, coupling an EMI shielded gasket having a rod to a hinge side of the frame and a hinge side of the closing structure, and attenuating EMI signals passing through a slot between the closing structure and the frame to shield an edge of the opening of the EMI shielded enclosure.

The foregoing has outlined generally the features of the present disclosure in order that the detailed description that follows can be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific aspects of the disclosure, wherein.

DETAILED DESCRIPTION

Figure 1:
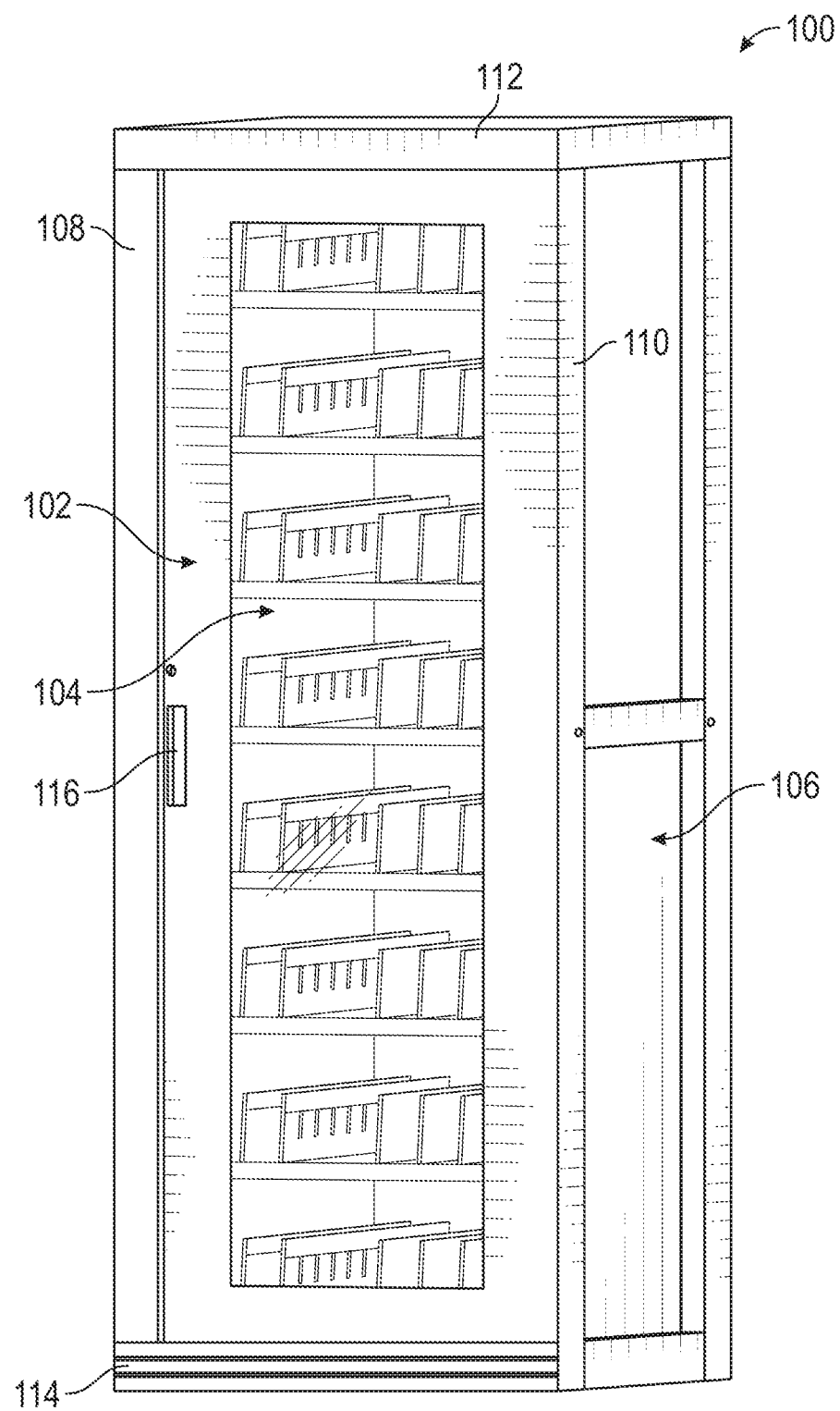
FIG. 1 illustrates a front view of an example supply cabinet, according to some aspects of the disclosure.

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and can be practiced using one or more implementations. In one or more instances, well-known structures and components are shown in block diagram form in order to avoid obscuring the concepts of the subject technology.

According to some implementations, the subject technology provides a door assembly for a supply cabinet such as a medical supply cabinet. The supply cabinet can be used for storing supply items. In some examples, the supply cabinet can be used for storing medical supplies. The items may be equipped with RFID tags or other tags that can be invoked by transmitting RF energy, e.g., RF signals. The supply cabinet may be equipped with RF transmitter for sending RF signals to read RFID tags as well as a receiver and/or detector to receive the RF signals back from the items and to detect the RFID tags. The receiver may keep an inventory of the items inside the supply cabinet. Therefore, it is desirable that the transmitter does not send RF signal outside the supply cabinet.

In some instances, it is desirable that the receiver does not receive RF signals from outside the supply cabinet. Thus, the supply cabinet body including the sides, the back, the top and bottom, and the door may be shielded against EMI such that RF energy is considerably attenuated when passing through the body the supply cabinet. However, RF signals may get through the opening that may exist between a cabinet door and the body of the supply cabinet.

In some examples, the supply cabinet includes a doorframe, and the door is connected to the doorframe. Openings may exist between the doorframe and the cabinet door. In some examples, the cabinet door includes a first surface facing an inside of the supply cabinet and a second surface opposite to the first surface and facing an outside of the supply cabinet. Around the doorframe, one or more enclosure brackets may be mounted. The enclosure brackets may extend outside of the cabinet enclosure. The first surface of the cabinet door facing the inside of the supply cabinet may have an outer border area and a recessed inner border area, surrounded by the outer border area. The outer border area may extend to the edges of the cabinet door. In some examples, the enclosure brackets may be received in the recessed inner border area when the door is closed.

One or more finger bracket structures may be mounted in the recessed inner border area next to the outer border area, with a clearing distance of a predetermined length from the outer border area. The finger bracket structure may comprise a bracket and one or more finger gaskets coupled to the bracket. The one or more finger gaskets of the one or more finger brackets structure may extend in the clearing distance and may touch the enclosure brackets that are received in the recessed area when cabinet door is closed. The combination of the enclosure brackets and the finger bracket structures touching each other in the recessed area may provide a primary mechanism to seal the cabinet door of the supply cabinet. The combination may highly attenuate RF energy existing from the opening between the doorframe and the cabinet door.

In some embodiments, a first type of a secondary barrier may exist on the vertical hinge of the cabinet door to seal the cabinet door. The second barrier may be made of fabric over foam and may extend from a top of the cabinet door to the bottom of the cabinet door. The second barrier may further attenuate RF energy that may exit, e.g., escape, or enter from the hinge-side of the cabinet door. In some embodiments, a second type of secondary barrier may exist in the form of an RF fence bracket at the latch-side of the cabinet door. The RF fence bracket may extend from top of the doorframe to bottom of the doorframe. An edge of the RF fence bracket can create a narrowing with an edge of the cabinet door at the latch-side of the doorframe to make it difficult for RF energy to exit or enter from the latch-side of the cabinet door.

FIG. 1 illustrates a front view of an example supply cabinet, according to some aspects of the disclosure. As shown, a supply cabinet 100 of FIG. 1 includes a hinge-side cabinet wall 106 and a cabinet door structure 102 having a latch 116 and a clear cabinet window 104. In some examples, cabinet door structure 102 is mounted via a doorframe to supply cabinet 100. The doorframe may include a latch-side portion 108, a hinge-side portion 110, a top-side portion 112, and a bottom-side portion 114. As the door may swing open, there may be an opening between the doorframe and cabinet door structure 102. In some examples, hinge-side portion 110 of the doorframe is coupled to a hinge-side of the cabinet door structure 102 and latch-side portion 108 of the doorframe is configured to couple to a latch-side of the cabinet door structure 102. In some embodiments, the doorframe is mounted around the edge of an opening of cabinet enclosure 210 and enclosure brackets 202 that are coupled to one or more sides of the doorframe extend outside of cabinet enclosure 210. In some examples, a door assembly includes cabinet door structure 102 and the doorframe coupled to cabinet door structure 102.

Figure 2:
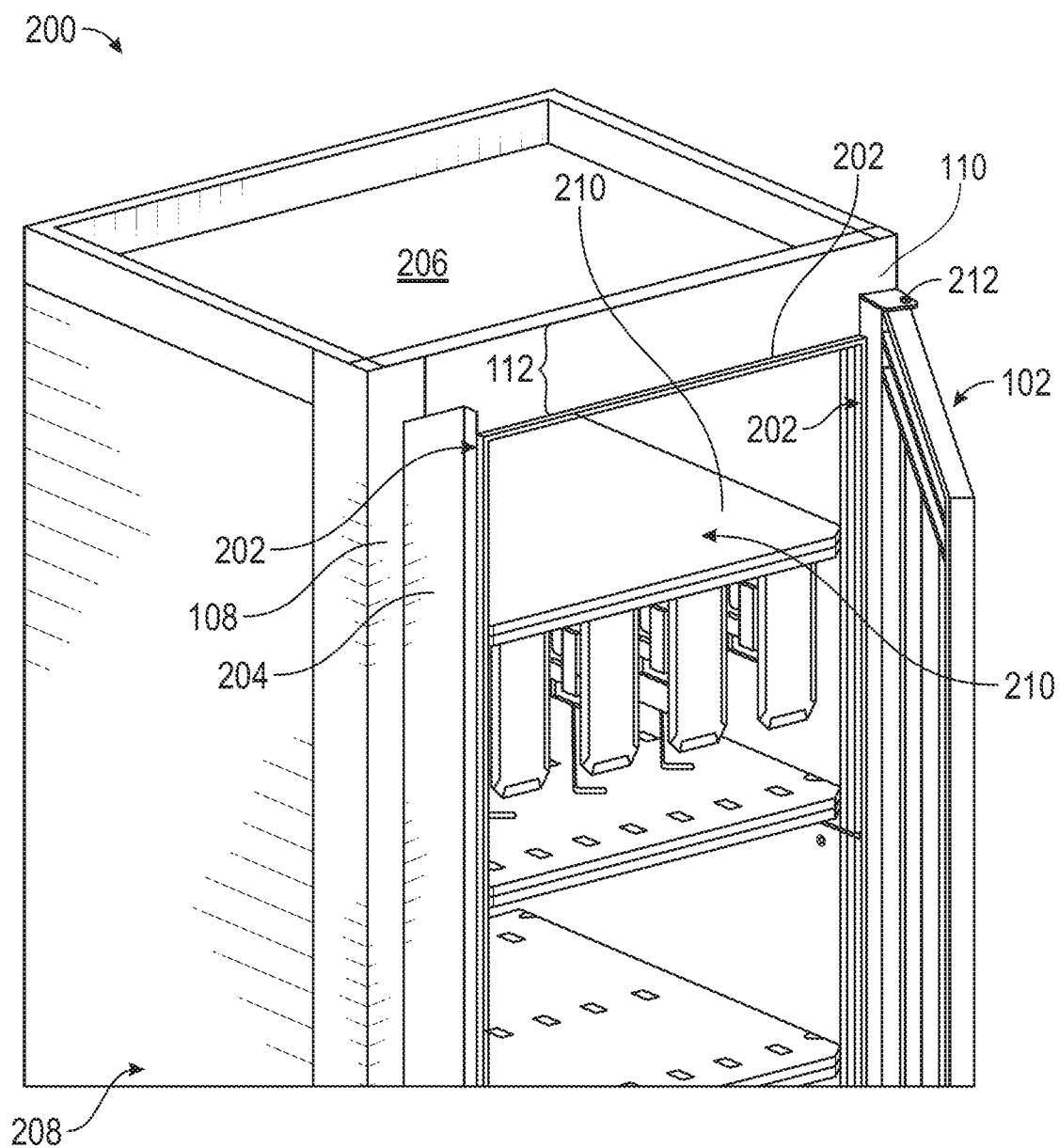
FIG. 2 illustrates a top view of an example supply cabinet with ajar door, according to some aspects of the disclosure.

FIG. 2 illustrates a top view of an example supply cabinet with an ajar door, according to some aspects of the disclosure. As shown supply cabinet 200 of FIG. 2, that is consistent with supply cabinet 100 of FIG. 1, includes cabinet door structure 102, top-side 206 of supply cabinet, and latch-side cabinet wall 208 of supply cabinet. As shown, cabinet door structure 102 is open and cabinet enclosure 210 is accessible. Supply cabinet 200 also shows top-side portion 112 of doorframe and latch-side portion 108 of doorframe that are coupled around the opening of cabinet enclosure 210. In some examples, hinge-side portion 110 of doorframe (FIG. 1) is coupled to a hinge-side of cabinet door structure 102 via hinge rod 212. Additionally, shown in FIG. 2, are enclosure brackets 202, which extend outward from edges of the doorframe. Enclosure brackets 202 are coupled to the hinge-side portion 110 of the doorframe, the latch-side portion 108 of doorframe, and the top-side portion 112 of doorframe. In addition, one or more enclosure brackets 202 may be coupled to the bottom-side portion 114 (not shown) of doorframe. Enclosure brackets 202 are described in more details with respect to FIGS. 5-10. In some embodiments, bracket 204 is mounted on the latch-side portion 108 of doorframe. Bracket 204 is described in more details with respect to FIG. 5.

Figure 3:
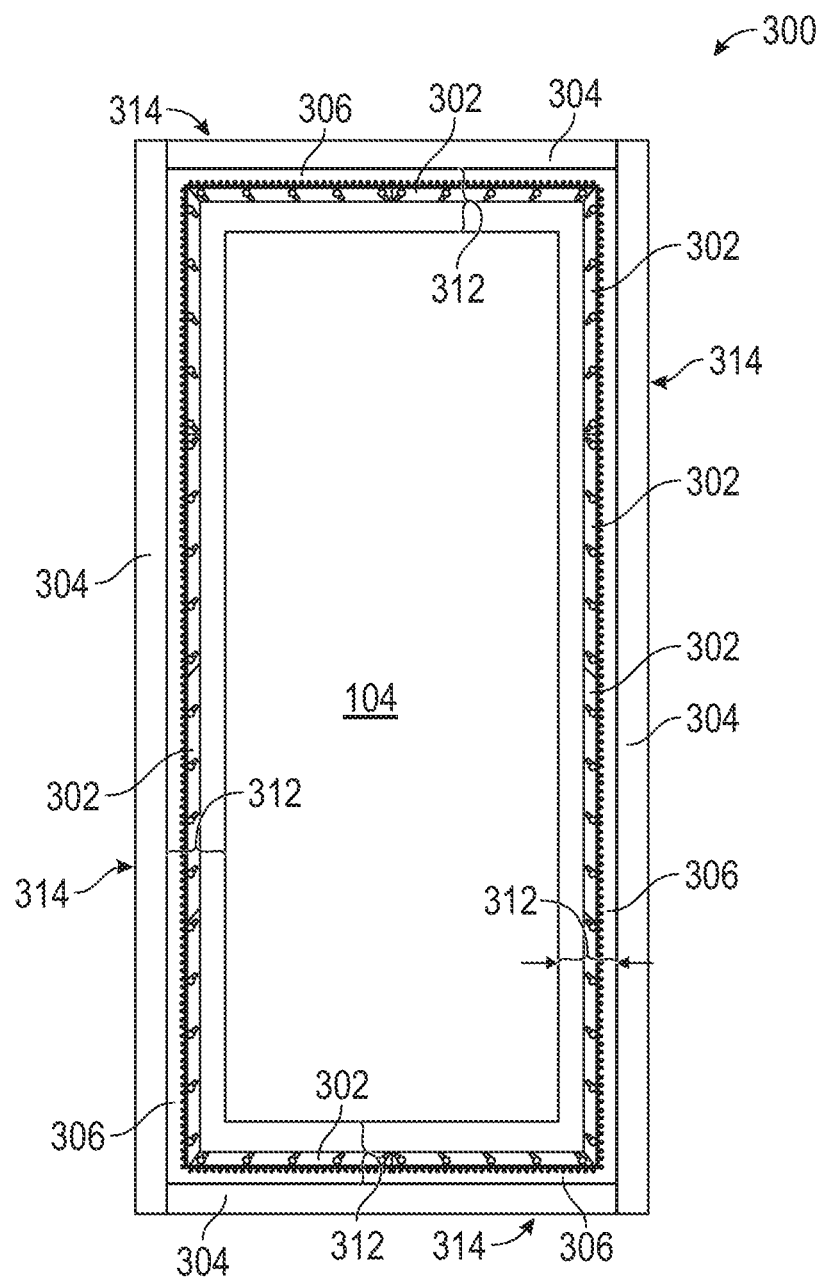
FIG. 3 illustrates a front view of an inside surface of an example cabinet door structure, according to some aspects of the disclosure.

FIG. 3 illustrates a front view of an inside surface of an example cabinet door structure, according to some aspects of the disclosure. FIG. 3 shows an inside surface 300 of cabinet door structure 102 of FIGS. 1 and 2 that is configured to face an inside of supply cabinet 100. One or more finger bracket structures 302 are coupled to inside surface 300 of cabinet door structure 102. In some examples, outer border area 304, which may be elevated, compared to the rest of inside surface 300, is next to edges 314 of the cabinet door structure 102. In some examples, a recessed inner border area 312 is recessed compared to the outer border area 304, and may form a recessed inner border area, positioned between the cabinet window 104 and the outer border area 304. Finger bracket structures 302 may be coupled to the inner border area 312 and next to the outer border area 304 with a clearing distance 306 of a predefined length between the finger bracket structures 302 and the outer border area 304. In each side of cabinet door structure 102 there may be more than one finger bracket structure 302 coupled serially, side by side about the door structure 102. Finger bracket structures 302, as shown in FIG. 3, may be adjusted in position in left-to-right/right-to-left and up-to-down/down-to-up directions. The clearing distance 306 and finger bracket structures 302 are described in more details with respect to FIGS. 4-10.

Figure 4:
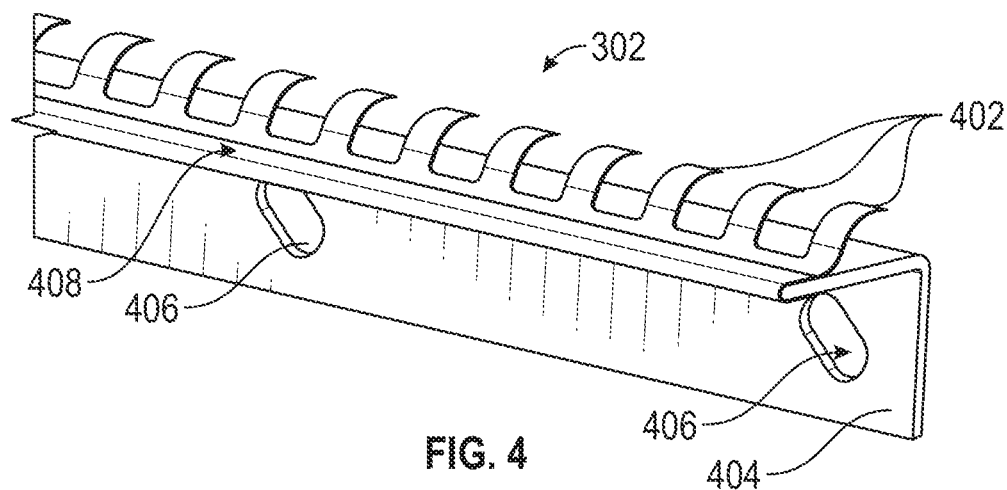
FIG. 4 illustrates an example finger bracket structure, according to some aspects of the disclosure.

As shown in FIG. 4, in some embodiments, one or more finger gaskets 402 of the one or more finger bracket structures 302 of FIG. 3 may contact one or more enclosure brackets 202 of FIG. 2. The finger bracket structures 302 may contact enclosure brackets 202 around an edge of the opening of the cabinet enclosure 210 when the door structure is closed. A combination of the finger gaskets 402 in contact with the enclosure brackets 202 may create an electromagnetic interference (EMI) shield at the edge of the opening of cabinet enclosure 210. In some examples, enclosure brackets 202 are Electroless Nickel plated to prevent corrosion and wear.

FIG. 4 illustrates an example finger bracket structure, according to some aspects of the disclosure. As shown, finger bracket structure 302 of FIG. 4 includes finger gasket structure 408 that includes a plurality of finger gaskets 402. Additionally, finger brackets structure of 302 includes bracket 404 that may include one or more slotted holes 406. As shown by inside surface 300 of FIG. 3, there may be one or more finger bracket structures 302 on each side of the cabinet door structure. Finger bracket structures 302 can be adjusted in place through slotted holes 406 via screws and/or nuts and bolts that attach finger bracket structures to the inside surface of cabinet door structure 102. In some examples, the finger gaskets 402 of the finger bracket structures 302 are made from Beryllium Copper and are Electroless Nickel plated to reduce or limit corrosion and wear. In some examples, after brackets 404 are adjusted in place, finger gasket structures 408 may be clipped into adjusted brackets 404. In some embodiments, finger gasket structure 408 may include a body that folds around an edge of bracket 404. In some examples, finger gasket structure 408 may include a narrow body that is attached to a face of bracket 404.

Figure 5:
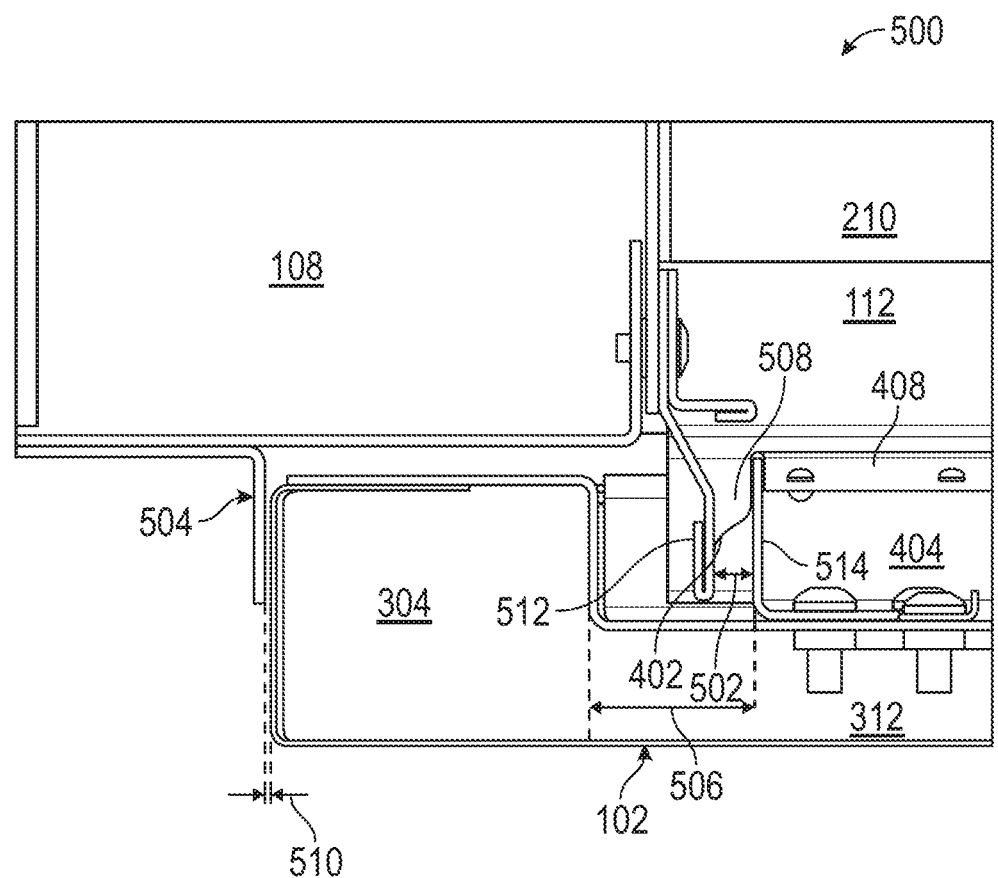
FIG. 5 illustrates a top view at the latch-side of an example cabinet door structure, according to some aspects of the disclosure.

FIG. 5 illustrates a top view at the latch-side of an example cabinet door structure, according to some aspects of the disclosure. As shown latch-side view 500 of FIG. 5 shows cabinet door structure 102, latch-side portion 108 of doorframe, and cabinet enclosure 210. Cabinet door structure 102 includes outer border area 304 and inner border area 312 that is recessed compared to outer border area 304. Latch-side view 500 also shows a first finger bracket structure that is bolted to a top portion of inner border area 312. The first finger bracket structure includes bracket 404 and finger gasket structure 408. In some examples, latch-side view 500 is a top view and thus may illustrate a top view of a second finger bracket structure that is bolted to a latch-side portion of inner border area 312 from top to bottom of the inner surface of cabinet door structure 102. Thus, latch-side view 500 shows a top view of the second finger bracket structure that includes finger gasket 402 that is coupled to bracket 514 that is consistent with bracket 404. Latch-side view 500 also includes latch-side clearing distance 506 that is consistent with clearing distance 306 of FIG. 3 between bracket 514 and outer border area 304. Clearing distance 506 may be adjusted through nuts and bolts that attach bracket 514 to the inner border area 312.

In some embodiments, latch-side view 500 includes enclosure bracket 508 that is consistent with enclosure bracket 202 of FIG. 2, extends along top-side portion 112 of doorframe, and protrudes out of the cabinet enclosure 210. Enclosure bracket 508 may be coupled to top-side portion 112 of doorframe as shown in FIG. 2. In some examples, finger gasket structure 408 of the first finger bracket structure comes into contact with enclosure bracket 508 in a clearing distance (not shown) at the top of the door when cabinet door structure 102 closes. In some embodiments as shown in FIG. 5, bracket 404 of the first finger bracket structure that is coupled to top portion of inner border area 312 may come into contact with bracket 514. In some embodiments, as shown in FIG. 5, bracket 514 of the second finger bracket structure that is coupled to latch-side portion of inner border area 312 has no clearing distance with bracket 404. In some examples, a distance in the order of a width of finger gasket 402 may exist between brackets 404 and 514.

Also shown is a top view of enclosure bracket 512 that is consistent with enclosure bracket 202, extends along latch-side portion 108 of doorframe, and protrudes out of cabinet enclosure 210. Enclosure bracket 512 may be coupled to latch-side portion 108 of doorframe as shown in FIG. 2 and may protrude from the doorframe into the clearing distance 506 and may come into contact with finger gasket 402 when cabinet door structure 102 closes. As described, enclosure bracket 512 as well as bracket 514 may extend along latch-side portion 108 of doorframe from top to bottom of supply cabinet. Bracket 514 may include a plurality of finger gaskets 402 that also extend along latch-side portion 108 of doorframe and when cabinet door structure 102 closes, the plurality of finger gaskets 402 come into contact with enclosure bracket 512. In addition, RF fence bracket 504 that is consistent with bracket 204 of FIG. 2 may be coupled to latch-side portion 108 of doorframe and extends along latch-side portion 108 of doorframe from top to bottom. When cabinet door structure 102 closes a narrow path, RF fence gap 510, may be created between cabinet door structured 102 and RF fence bracket 504. In some examples, RF signals passing through the narrow path may be attenuated and an EMI shield may be created at the latch-side of the EMI shielded cabinet enclosure.

Figure 6:
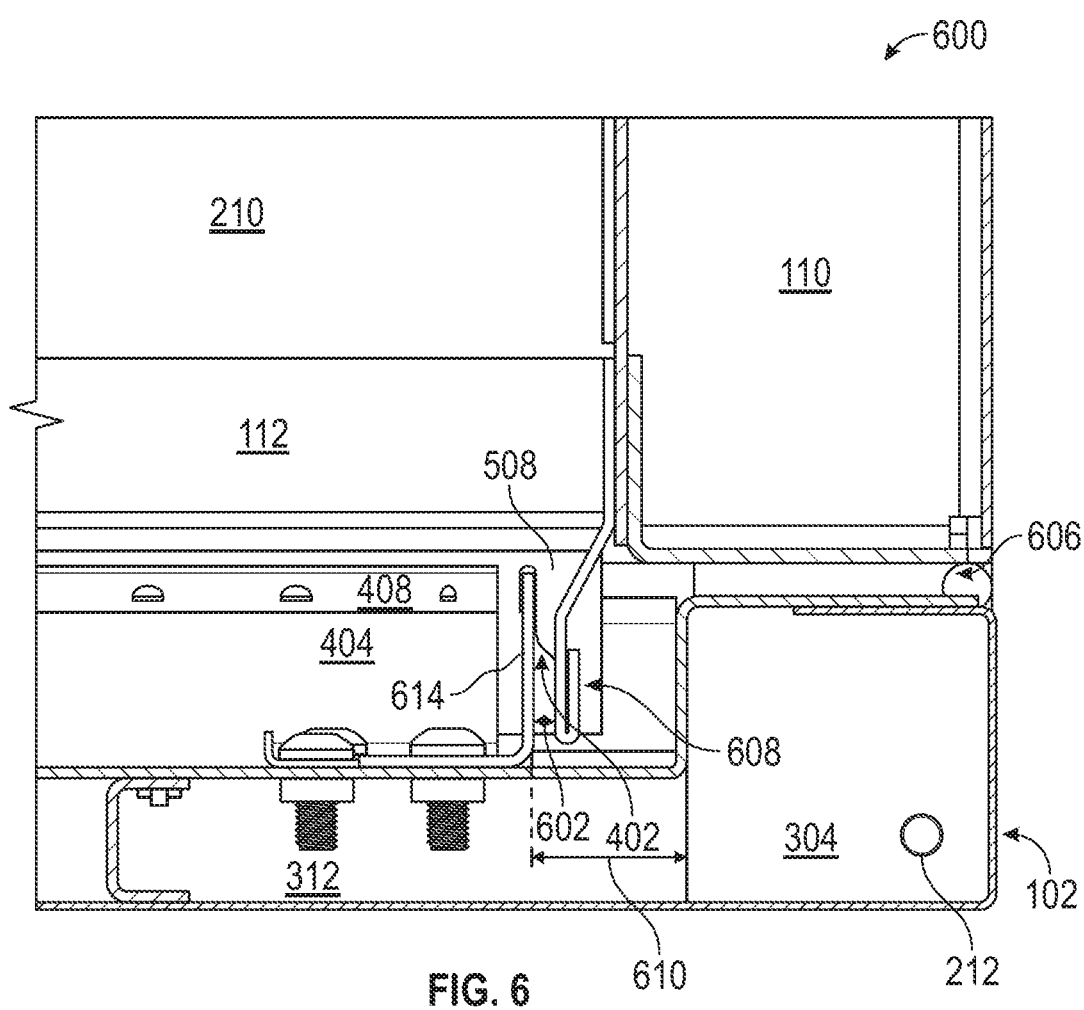
FIG. 6 illustrates a top view at the hinge-side of an example cabinet door structure, according to some aspects of the disclosure.

FIG. 6 illustrates a top view at the hinge-side of an example cabinet door structure, according to some aspects of the disclosure. As shown, hinge-side view 600 of FIG. 6 shows cabinet door structure 102, hinge-side portion 110 of doorframe, and cabinet enclosure 210. Hinge-side view 600 shows hinge rod 212 of FIG. 2 that cabinet door structure 102 may swing around hinge rod 212 to open or close. Cabinet door structure 102 includes outer border area 304 and inner border area 312 that is recessed compared to outer border area 304. Hinge-side view 600 also shows the first finger bracket structure that is bolted to the top portion of inner border area 312. The first finger bracket structure includes bracket 404 and finger gasket structure 408. In some examples, hinge-side view 600 is a top view and thus may illustrate a top view of a third finger bracket structure that is bolted to a hinge-side portion of inner border area 312 from top to bottom of the inner surface of cabinet door structure 102. Thus, hinge-side view 600 shows a top view of the third finger bracket structure that includes finger gasket 402 that is coupled to bracket 614 that is consistent with bracket 404 of FIG. 4. Hinge-side view 600 also includes hinge-side clearing distance 610 that is consistent with clearing distance 306 of FIG. 3 between bracket 614 and outer border area 304. Clearing distance 610 may be adjusted through nuts and bolts that attach bracket 614 to the inner border area 312. In some embodiments, bracket 404 that is coupled to top portion of inner border area 312 may come into contact with bracket 614 of the third finger bracket structure that is coupled to hinge-side portion of inner border area 312. In some examples, as shown in FIG. 6, a distance in the order of a width of finger gasket 402 may exist between brackets 404 and 614.

In some embodiments, hinge-side view 600 includes enclosure bracket 508 that is also shown in latch-side view 500 of FIG. 5. Enclosure bracket 508 extends along top-side portion 112 of doorframe, and protrudes out of the cabinet enclosure 210. In some examples, as shown in FIG. 6, finger gasket structure 408 of the first finger bracket structure comes into contact with enclosure bracket 508 in a clearing distance at the top of the door when cabinet door structure 102 closes.

Also shown in FIG. 6 is a top view of enclosure bracket 608 that is consistent with enclosure bracket 202, extends along hinge-side portion 110 of doorframe, and protrudes out of supply cabinet. Enclosure bracket 608 may be coupled to hinge-side portion 110 of doorframe and may protrude from the doorframe into the clearing distance 610. Enclosure bracket 608 may come into contact with finger gasket 402 when cabinet door structure 102 closes. As described, enclosure bracket 608 as well as bracket 614 of the third finger bracket structure may extend along hinge-side portion 110 of doorframe from top to bottom of cabinet enclosure 210. Bracket 614 may include a plurality of finger gaskets 402 that also extend along hinge-side portion 110 of doorframe and when cabinet door structure 102 closes, the plurality of finger gaskets 402 come into contact with enclosure bracket 608. In some embodiments, rod 606 of a semi-cylindrical shape that may be made of fabric-over-foam and may act as EMI shielded gasket is coupled to hinge-side of cabinet door structure. Rod 606 may extend parallel to the hinge-side from top to bottom of supply cabinet and may be coupled between the hinge-side 110 of doorframe and cabinet door structure 102. In some embodiments, rod 606 is shielded from contacting a metal surface when cabinet door structure 102 is opened or is closed. Rod 606 may reduce a slot between the cabinet door structure 102 and doorframe to shield the edge of the opening of the cabinet enclosure 210, e.g., to shield the edge of the EMI shielded cabinet enclosure.

In some embodiments, cabinet enclosure 210 may be sealed against EMI such that RF signals may not leak out of cabinet enclosure 210 or vice a versa. A body of supply cabinet 100 shown in FIG. 1, including cabinet door structure 102 and cabinet window 104, may be made of a material that essentially prevents RF energy from passing through the supply cabinet body.

Leakage paths may exist around cabinet door structure 102 and EMI may exist due to leakage paths around cabinet door structure 102. To reduce leakage of RF energy, the primary EMI barrier is the enclosure brackets that come into contact with finger bracket structures. The enclosure brackets 202 may touch finger gasket structures 408 and finger gaskets 402 in the clearing distances between the finger bracket structures and outer border area 304 at top, bottom, and the two sides of cabinet door structure 102 to shield the edge of the opening of the cabinet enclosure 210.

Secondary EMI barriers may exist along latch-side portion 108 of doorframe and along hinge-side portion 110 of doorframe between cabinet door structure 102 and cabinet enclosure 210. RF fence gap 510 is designed to be a narrow gap to create a torturous path as a secondary EMI barrier at the latch-side to hinder RF energy leakage along the latch-side of the cabinet door structure 102. Rod 606 may act as a secondary EMI barrier at the hinge-side of cabinet door structure 102.

In some embodiments, it is important to limit the leakage of RF energy and at the same time make sure that cabinet door structure 102 can easily be opened or closed. Therefore, in some examples, RF fence gap 510 is set at a predetermined distance between 0.01 inches to 0.03 inches, e.g., 0.02 inches to keep the RF fence gap 510 small and at the same time to prevent RF fence bracket 504 from touching cabinet door structure 102 and minimize door closing/opening forces. In addition, escape gap 502 may exist in the latch-side portion of inner border area 312 between bracket 514 and enclosure bracket 512. Escape gap 502 may be kept between 0.35 inches to 0.55 inches, e.g., 0.45 inches to make sure finger gaskets 402 of bracket 514 may touch enclosure bracket 512 and minimize/reduce door closing/opening forces. In some embodiments, finger gasket structure 408 of first finger bracket structure is coupled to bracket 404 such that when cabinet door structured 102 closes finger gaskets 402 of finger gasket structure 408 touch enclosure bracket 508. The touching of finger gasket 402 with enclosure bracket 508 may prevents RF energy leakage from top portion of supply cabinet 100 of FIG. 1. In some embodiments, a similar finger bracket structure may exist at a bottom portion of inner border area 312 of cabinet door structure 102 to prevent RF energy leakage from bottom of supply cabinet 100 of FIG. 1. In some embodiments, a similar escape gap in inner border area 312 may have a width between 0.35 inches to 0.55 inches, e.g., 0.45 inches, at top and bottom portions of inner border area 312. The escape gap width may be selected to make sure finger gaskets 402 of finger bracket structures 408 coupled to the top and bottom portions of inner border area 312 may touch enclosure bracket 202 protruding from top-side portion 112 and bottom-side portion 114 of doorframe. In addition, the escape gap width may be selected to minimize door closing/opening forces.

Figure 7:
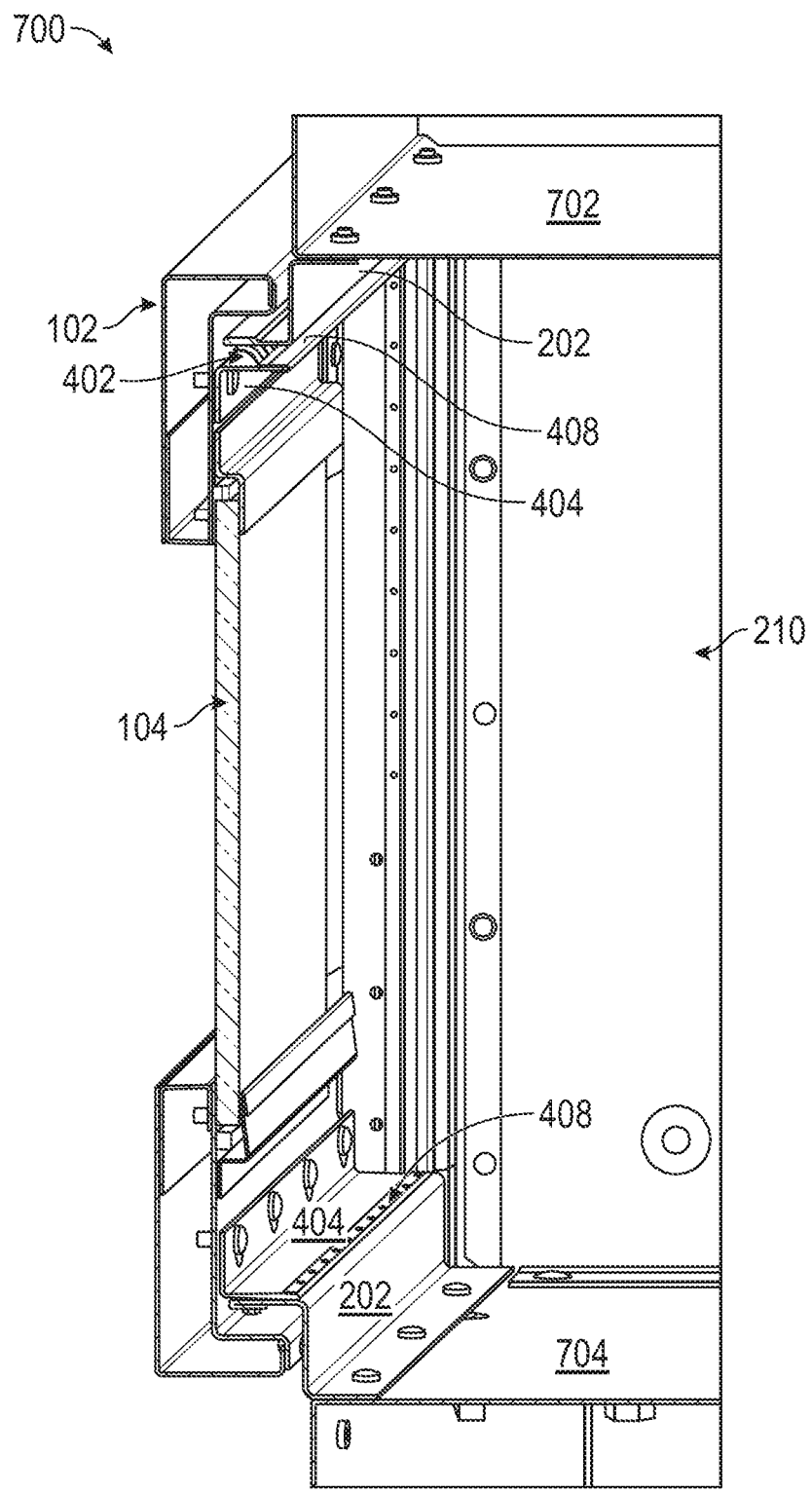
FIG. 7 illustrates a side cutaway view of an example supply cabinet, according to some aspects of the disclosure.

FIG. 7 illustrates a side cutaway view of an example supply cabinet, according to some aspects of the disclosure. As shown, cutaway view 700 of supply cabinet of FIG. 7 that is consistent with supply cabinet 100 of FIG. 1 includes top EMI barrier 702 and bottom EMI barrier 704 that are respectively located on top and bottom of cabinet enclosure 210 and may shield cabinet enclosure 210 from RF signals. Also shown in FIG. 7 enclosure bracket 202 coupled to top EMI barrier 702 and another enclosure bracket 202 coupled to bottom EMI barrier 704. Also shown at the top and bottom of FIG. 7 are finger bracket structures coupled to cabinet door structure 102. The finger bracket structures include brackets 404 and finger gasket structures 408 that are in contact with enclosure brackets 202 via finger gaskets 402.

Figure 8:
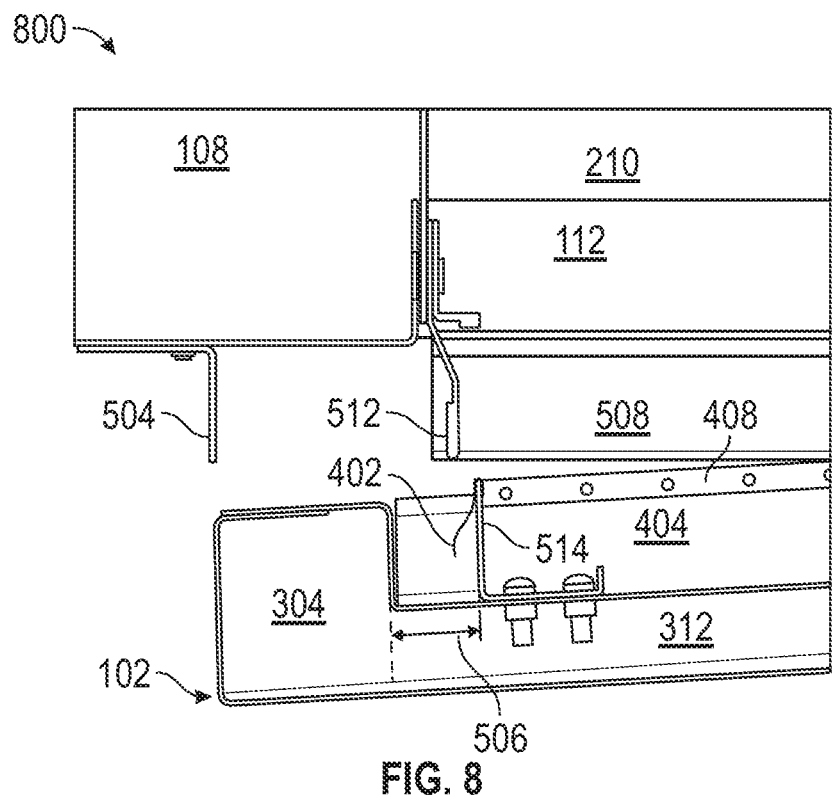
FIG. 8 illustrates a top view at the latch-side of an example cabinet door structure with door ajar, according to some aspects of the disclosure.

FIG. 8 illustrates a top view at the latch-side of an example cabinet door structure, according to some aspects of the disclosure. As shown, latch-side 800 essentially includes same elements shown in FIG. 5 with the difference that cabinet door structure 102 is slightly open. As shown in FIG. 8, by opening cabinet door structure 102 finger gasket 402 separated from enclosure bracket 512 and RF fence bracket 504 may be separated from cabinet door structure 102. Additionally, finger gasket structure 408 may be separated from enclosure bracket 508.

Figure 9:
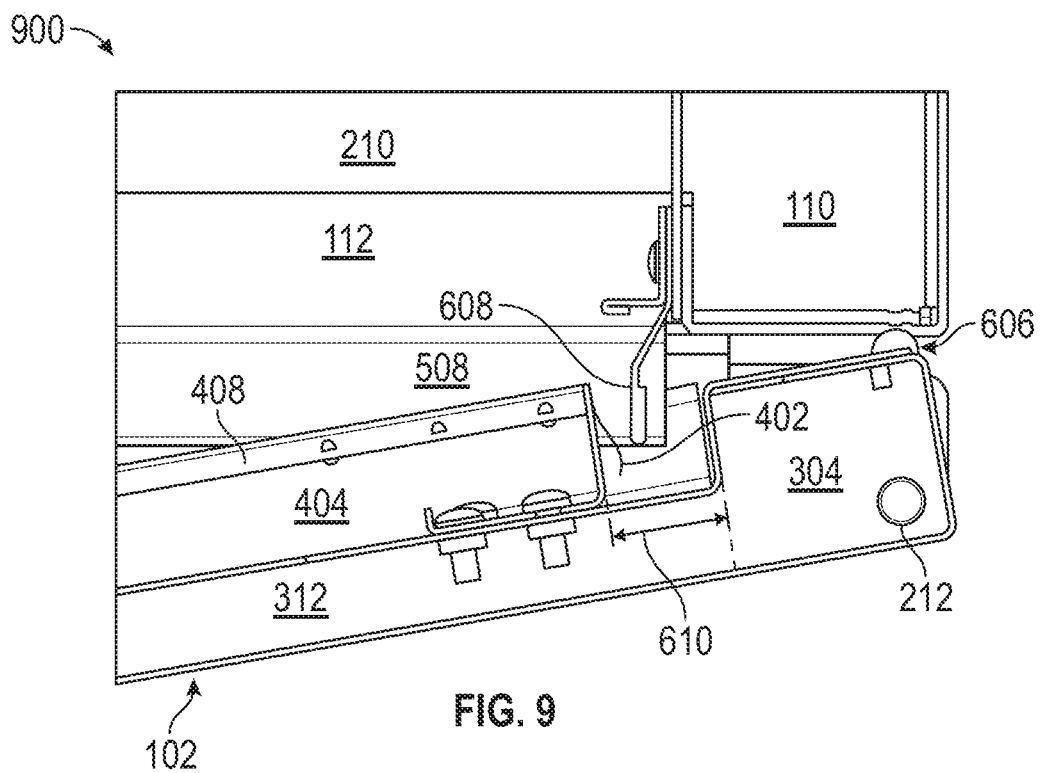
FIG. 9 illustrates a top view at the hinge-side of an example cabinet door structure with door ajar, according to some aspects of the disclosure.

FIG. 9 illustrates a top view at the hinge-side of an example cabinet door structure, according to some aspects of the disclosure. As shown, hinge-side 900 essentially includes same elements shown in FIG. 6 with the difference that cabinet door structure 102 is a slightly open. As shown in FIG. 9, by opening cabinet door structure 102 finger gasket 402 may be separated from enclosure brackets 608. Additionally, finger gasket structure 408 may be separated from enclosure bracket 508.

Figure 10:
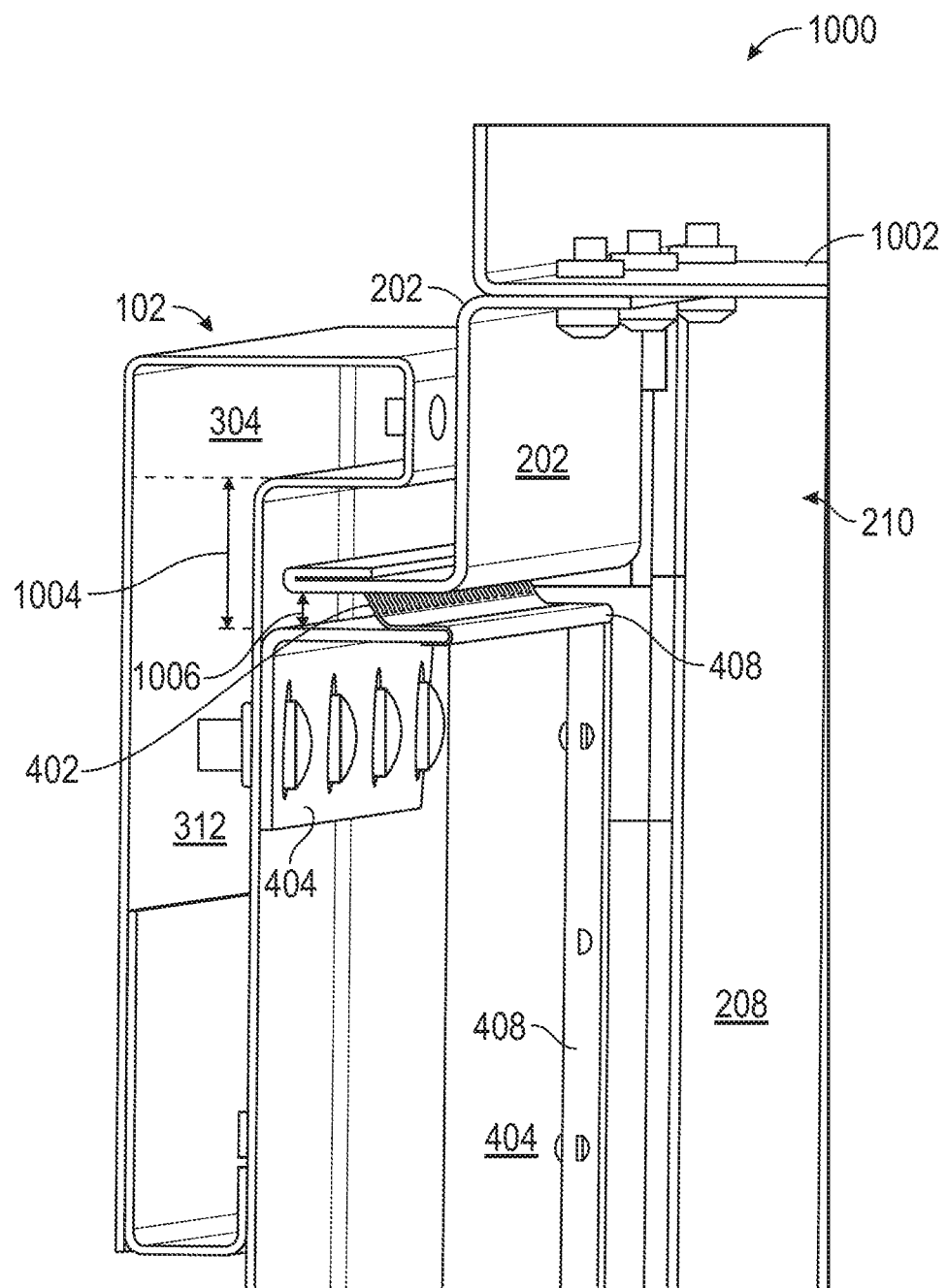
FIG. 10 illustrates a side cutaway view of an example supply cabinet, according to some aspects of the disclosure.

FIG. 10 illustrates a side cutaway view of an example supply cabinet, according to some aspects of the disclosure. As shown, cutaway view 1000 of supply cabinet of FIG. 10 that is consistent with supply cabinet 100 of FIG. 1 includes top EMI barrier 1002 that is consistent with EMI barrier 702 of FIG. 7 and is located at the top of cabinet enclosure 210. Cutaway view 1000 also includes enclosure bracket 202 that is coupled to EMI barrier 1002. Also shown are cabinet door structure 102 and a finger bracket structure that is coupled to cabinet door structure 102. The finger bracket structure that includes finger gasket structure 408 coupled to bracket 404 may be in contact with enclosure brackets 202 via finger gaskets 402. The cabinet door structure 102 includes outer border area 304 and inner border area 312. The finger bracket structure is coupled to top portion of inner border area 312. Also shown in FIG. 10 are clearing distance 1004 between outer border area 304 and bracket 404 of the finger bracket structure as well as escape gap 1006 between the bracket 404 and enclosure bracket 202. In some examples, FIG. 10 is a close-up view, at top portion, of FIG. 7.

Figure 11:
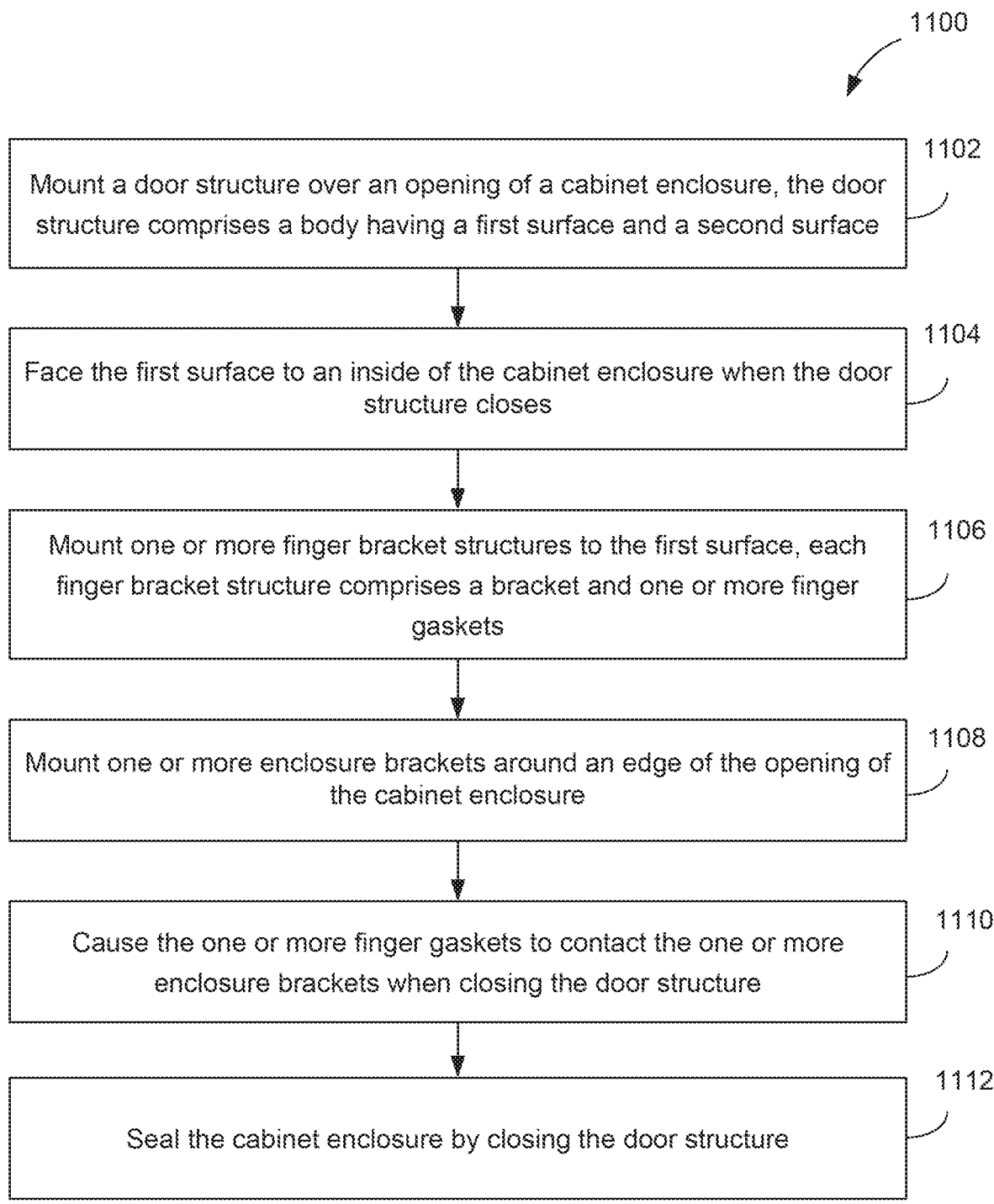
FIG. 11 illustrates a flow diagram of an example process of sealing a supply cabinet, according to some aspects of the disclosure.

FIG. 11 illustrates a flow diagram of an example process of sealing a supply cabinet, according to some aspects of the disclosure. Notably, one or more steps of process 1100 described herein may be omitted, performed in a different sequence, and/or combined with other processes for various types of applications contemplated herein. Process 1100 can be performed to seal supply cabinets 100 and 200 of FIGS. 1 and 2.

The process 1100 begins at step 1102; a door structure is mounted over an opening of the cabinet enclosure. The door structure comprises a body having a first interface and a second interface. As shown in FIG. 2, cabinet door structure 102 is mounted over cabinet enclosure 210. In some examples, the cabinet enclosure is an EMI shielded cabinet enclosure and cabinet door structure 102 includes an EMI shielded body. Cabinet door structure 102 may include a first surface and the second surface opposite to the first surface.

In step 1104, the first surface is faced to the inside of cabinet enclosure 210 when cabinet door structure 102 closes. As shown in FIG. 2, door structure 102 has a first surface that when cabinet door structure 102 closes faces inside of cabinet enclosure 210 that may be an EMI shielded cabinet enclosure.

In step 1106, one or more finger bracket structures are mounted to the first surface. Each finger bracket structure may comprise a bracket and one or more finger gaskets. As shown in FIG. 3, finger bracket structures 302 are mounted to inside surface 300 of cabinet door structure 102. As shown in FIG. 4, each finger bracket structure 302 includes bracket 404 and one or more finger gaskets 402. In some examples, two or more finger gaskets 402 are coupled to create finger gasket structure 408.

In step 1108, one or more enclosure brackets are mounted around an edge of the opening of the cabinet enclosure 210 that may be an EMI shielded cabinet enclosure. As shown in FIG. 2, enclosure brackets 202 are coupled to edges of cabinet enclosure 210. In some embodiments, enclosure brackets 202 are coupled to a doorframe mounted around the edges of cabinet enclosure 210. In some examples, enclosure bracket 202 may protrude outside cabinet enclosure 210. Also, as shown in FIG. 5, enclosure bracket 508 that is coupled to top-side portion 112 of doorframe and protrudes inside a clearing distance at the top portion of inner border area 312. Additionally, enclosure brackets 512 that is coupled to the latch-side portion 108 of doorframe protrudes to clearing distance 506 at the latch-side portion of inner border area 312. As shown in FIG. 6, enclosure bracket 508 that is coupled to top-side portion 112 of doorframe may protrude inside the clearing distance (not shown) at the top portion of inner border area 312. Additionally, enclosure brackets 608 that is coupled to the hinge-side portion 110 of doorframe protrudes to clearing distance 610 at the hinge-side portion of inner border area 312.

In step 1110, one or more finger gaskets are caused to come into contact with one or more enclosure brackets when closing the door structure. As shown in FIG. 5, by closing the cabinet door structure 102, enclosure bracket 512 comes into contact with one or more finger gaskets 402, which creates an EMI shield at the latch-side portion 108 of doorframe between the doorframe and cabinet door structure 102. Additionally, finger gaskets 402 (not shown) of finger gasket structure 408 at the top portion of inner border area 312 come into contact with enclosure bracket 508, which creates an EMI shield at top-side portion 112 of doorframe between the doorframe and cabinet door structure 102. As shown in FIG. 6, by closing cabinet door structure 102, enclosure bracket 608 comes into contact with one or more finger gaskets 402, which creates an EMI shield at the hinge-side portion 110 of doorframe between the doorframe and cabinet door structure 102. Similarly, an EMI shield may be created at bottom-side portion 114 of doorframe between the doorframe and cabinet door structure 102.

In step 1112, cabinet enclosure is sealed by closing the door structure. As described, cabinet enclosure 210 may be EMI shielded. Additionally, a body of cabinet door structure 102 may also be EMI shielded. In some examples, there may be small openings between cabinet door structure 102 and one or more of hinge-side portion 110 of the doorframe, top-side portion 112 of doorframe, bottom-side portion 114 of doorframe, and latch-side portion 18 of doorframe. Thus, RF signals may pass through the openings between cabinet door structure 102 and one or more portions of doorframe and as a result, cabinet enclosure 210 may not be EMI shielded, e.g., may not be sealed from RF signals. As described above, by closing cabinet door structure 102 over cabinet enclosure 210, finger gaskets 402 come into contact with enclosure branch 202 at hinge-side portion 110, top-side portion 112, bottom-side portion 114, and latch-side portion 108 of the doorframe. Thus, the supply cabinet becomes EMI shielded.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "module for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

What is claimed is:

1. A shield assembly comprising:
    a closing structure configured to be mounted over an opening of an electromagnetic interference (EMI) shielded enclosure, the closing structure comprising:
        an inner surface configured to face an inside of the EMI shielded enclosure when the closing structure is closed; and
        a finger bracket structure mounted on the inner surface, the finger bracket structure comprising a bracket and one or more finger gaskets coupled to the bracket; and
    an EMI shielded gasket comprising a rod coupled to a frame disposed around the opening of the EMI shielded enclosure, wherein the rod is shielded from contacting a metal surface when the closing structure is open and when the closing structure is closed.

2. The shield assembly of claim 1, wherein the rod comprises a semi-cylindrical shape and is made of fabric over foam.

3. The shield assembly of claim 1, wherein the rod is coupled to a hinge side of the closing structure.

4. The shield assembly of claim 3, wherein the rod extends in parallel to the hinge side of the closing structure from top to bottom of the EMI shielded enclosure and is coupled between a hinge side of the frame and the closing structure.

5. The shield assembly of claim 1, wherein the rod reduces a slot between the closing structure and the frame, and wherein the rod is configured to shield an edge of the EMI shielded enclosure.

6. The shield assembly of claim 1, further comprising:
    a radio frequency (RF) transceiver inside the EMI shielded enclosure, wherein the RF transceiver is configured to transmit an RF signal to detect wirelessly activated tags inside the EMI shielded enclosure.

7. The shield assembly of claim 1, wherein the one or more finger gaskets are configured to contact one or more enclosure brackets mounted around an edge of the opening of the EMI shielded enclosure when the closing structure is closed, and wherein a combination of the one or more finger gaskets in contact with the one or more enclosure brackets is configured to create an EMI shield at the edge of the opening of the EMI shielded enclosure.

8. The shield assembly of claim 7, wherein the EMI shield at the edge of the opening of the enclosure is a primary EMI barrier, and wherein the rod comprises a secondary EMI barrier at a hinge side of the closing structure.

9. The shield assembly of claim 7, wherein the inner surface of the closing structure includes an outer border area and an inner recessed area surrounded by the outer border area, wherein the outer border area extends from the inner recessed area to an edge of the closing structure, wherein the finger bracket structure is mounted inside the inner recessed area next to the outer border area with a clearing distance of a predefined width between the finger bracket structure and the outer border area;

wherein the one or more enclosure brackets protrude outside the edge of the opening of the EMI shielded enclosure and when the closing structure is closed the one or more enclosure brackets extend into the clearing distance between the finger bracket structure and the outer border area; and wherein the one or more finger gaskets are configured to contact the one or more enclosure brackets in the clearing distance between the finger bracket structure and the outer border area to shield the edge of the opening of the EMI shielded enclosure.

10. The shield assembly of claim 1, wherein the closing structure includes an EMI shielded clear window.

11. The shield assembly of claim 1, wherein the closing structure comprises a body having the inner surface, and wherein the body is EMI shielded.

12. The shield assembly of claim 1, wherein the frame comprises a top side, a bottom side, a hinge side, and a latch side, wherein one or more enclosure brackets are coupled to at least one of the sides of the frame.

13. A method of sealing radio frequency (RF) signals inside an electromagnetic interference (EMI) shielded enclosure, the method comprising:

configuring a closing structure to be mounted over an opening of the EMI shielded enclosure, wherein the closing structure comprises an inner surface;

facing the inner surface to an inside of the EMI shielded enclosure when the closing structure closes;

mounting a finger bracket structure to the inner surface, wherein the finger bracket structure comprises a bracket and one or more finger gaskets coupled to the bracket;

mounting a frame around the opening of the EMI shielded enclosure;

coupling an EMI shielded gasket comprising a rod to a hinge side of the frame and a hinge side of the closing structure;

shielding the rod from contacting a metal surface when the closing structure is open;

shielding the rod from contacting a metal surface when the closing structure is closed; and attenuating EMI signals passing through a slot between the closing structure and the frame to shield an edge of the opening of the EMI shielded enclosure.

14. The method of claim 13, further comprising:

causing the one or more finger gaskets to contact one or more enclosure brackets mounted around the edge of the opening of the EMI shielded enclosure when the closing structure is closed; and creating an EMI shield at the edge of the opening of the enclosure with a combination of the one or more finger gaskets in contact with the one or more enclosure brackets.

15. The method of claim 14, further comprising:

forming a primary EMI barrier with the EMI shield at the edge of the opening of the enclosure; and forming a secondary EMI barrier with the rod at the hinge side of the closing structure.

16. The method of claim 14, wherein the inner surface of the closing structure includes an outer border area and an inner recessed area surrounded by the outer border area, wherein the outer border area extends from the inner recessed area to an edge of the closing structure, wherein the method further comprises:

mounting the finger bracket structure inside the inner recessed area next to the outer border area; and providing a clearing distance of a predefined width between the finger bracket structure and the outer border area.

17. The method of claim 16, further comprising:

arranging the one or more enclosure brackets to protrude outside the edge of the opening of the EMI shielded enclosure; and extending the one or more enclosure brackets into the clearing distance between the finger bracket structure and the outer border area when the closing structure closes.

18. The method of claim 13, further comprising:

providing an RF transceiver inside the EMI shielded enclosure; and transmitting an RF signal to detect wirelessly activated tags inside the EMI shielded enclosure.

\* \* \* \* \*